(12) United States Patent
Rausch et al.

(10) Patent No.: US 11,654,436 B2
(45) Date of Patent: May 23, 2023

(54) MICROWAVE HEATING DEVICE FOR LAB ON A CHIP

(71) Applicant: Seagate Technology LLC, Fremont, CA (US)

(72) Inventors: Tim Rausch, Farmington, MN (US); Edward Charles Gage, Lakeville, MN (US); Walter R. Eppler, Cranberry Township, PA (US); Gemma Mendonsa, Edina, MN (US)

(73) Assignee: SEAGATE TECHNOLOGY LLC, Fremont, CA (US)

( * ) Notice: Subject to any disclaimer, the term of this patent is extended or adjusted under 35 U.S.C. 154(b) by 117 days.

(21) Appl. No.: 17/397,162

(22) Filed: Aug. 9, 2021

(65) Prior Publication Data

US 2022/0048032 A1 Feb. 17, 2022

Related U.S. Application Data

(60) Provisional application No. 63/064,139, filed on Aug. 11, 2020.

(51) Int. Cl.
| | |
|---|---|
| *B01L 7/00* | (2006.01) |
| *B01L 9/00* | (2006.01) |
| *B01L 3/00* | (2006.01) |
| *C12Q 1/686* | (2018.01) |
| *B82Y 5/00* | (2011.01) |
| *B82Y 25/00* | (2011.01) |

(52) U.S. Cl.
CPC ........... *B01L 7/52* (2013.01); *B01L 3/502715* (2013.01); *B01L 9/527* (2013.01); *B01L 2200/027* (2013.01); *B01L 2300/087* (2013.01); *B01L 2300/1816* (2013.01); *B01L 2300/1866* (2013.01); *B82Y 5/00* (2013.01); *B82Y 25/00* (2013.01); *C12Q 1/686* (2013.01)

(58) Field of Classification Search
CPC ................ B01L 7/52; B01L 3/502715; B01L 3/502761; B01L 9/527; B01L 2200/027; B01L 2300/087; B01L 2300/1816; B01L 2300/1866; B82Y 5/00; B82Y 25/00; B82Y 30/00; C12Q 1/686
See application file for complete search history.

(56) References Cited

U.S. PATENT DOCUMENTS

| | | |
|---|---|---|
| 7,616,412 B2 | 11/2009 | Zhu et al. |
| 8,394,339 B2 | 3/2013 | Silverbrook et al. |
| 2015/0224505 A1 | 8/2015 | Jensen et al. |

(Continued)

OTHER PUBLICATIONS

Miralles, V.; Huerre, A.; Malloggi, F.; Jullien, M.-C. A Review of Heating and Temperature Control in Microfluidic Systems: Techniques and Applications. Diagnostics 2013, 3, 33-67.

(Continued)

*Primary Examiner* — Jennifer Wecker
*Assistant Examiner* — Alea N. Martin
(74) *Attorney, Agent, or Firm* — Westman, Champlin & Koehler, P.A.

(57) ABSTRACT

A microfluidic device for polymerase chain reaction (PCR) processing includes a platform with a microstructure with at least one reaction chamber, and a heating element. The heating element heats at least a part of the at least one reaction chamber. The heating element includes at least one spin torque oscillator (STO) configured to heat the at least a part of the at least one reaction chamber to one or more temperatures for PCR processing.

20 Claims, 4 Drawing Sheets

(56) References Cited

U.S. PATENT DOCUMENTS

2016/0199839 A1 7/2016 Bergstedt et al.
2017/0108384 A1 4/2017 Hasson et al.
2017/0304829 A1 10/2017 Andreyev et al.

OTHER PUBLICATIONS

Norian, H.; Field, R.; Kymissis, I; Shepard, K. An integrated CMOS quantitative-polymerase chain-reaction lab-on-chip for point-of-care diagnostics. Royal Society of Chemistry 2013.
Sumito Tsunegi, Kay Yakushiji, Akio Fukushima, Shinji Yuasa, and Hitoshi Kubota. Microwave emission power exceeding 10 μW in spin torque vortex oscillator. Appl. Phys. Lett. 109, 252402 (2016); https://doi.org/10.1063/1.4972305.
Mulpuri V. Rao, Jayna J. Shah, Jon Geist and Michael Gaitan. Microwave Dielectric Heating of Fluids in Microfluidic Devices. Chapter 8, http://dx.doi.org/10.5772/53881.
Jeffrey A. Gerbec, Donny Magana, Aaron Washington, and Geoffrey F. Strouse. Microwave-Enhanced Reaction Rates for Nanoparticle Synthesis J. Am. Chem. Soc.9vol. 127, No. 45, 2005.

Grid Points with STO Heater are Shown Shaded

MICROWAVE HEATING DEVICE FOR LAB ON A CHIP

CROSS-REFERENCE TO RELATED APPLICATION(S)

This application claims priority to U.S. provisional application No. 63/064,139, filed on Aug. 11, 2020, the content of which is hereby incorporated by reference in its entirety.

SUMMARY

In one embodiment, a microfluidic device for polymerase chain reaction (PCR) processing includes a platform with a microstructure with at least one reaction chamber, and a heating element. The heating element heats at least a part of the at least one reaction chamber. The heating element includes at least one spin torque oscillator (STO) configured to heat the at least a part of the at least one reaction chamber to one or more temperatures for PCR processing.

In another embodiment, a method of heating a polymerase chain reaction (PCR) solution in a lab on a chip (LOC) includes providing a reaction chamber on the LOC, providing the solution to the reaction chamber, and heating at least one part of the reaction chamber of the LOC. The heating of the at least one part of the reaction chamber is performed using at least one spin torque oscillator (STO) configured to heat the PCR solution.

In another embodiment, a device includes a reaction chamber for polymerase chain reaction (PCR) processing of deoxyribonucleic acid (DNA), and a heating element for at least a part of the reaction chamber. The heating element includes at least one spin torque oscillator (STO) configured to heat the at least a part of the reaction chamber to one or more temperatures for PCR processing.

This summary is not intended to describe each disclosed embodiment or every implementation of PCR processing on LOCs using STOs as described herein. Many other novel advantages, features, and relationships will become apparent as this description proceeds. The figures and the description that follow more particularly exemplify illustrative embodiments.

DETAILED DESCRIPTION OF ILLUSTRATIVE EMBODIMENTS

Figure 1:
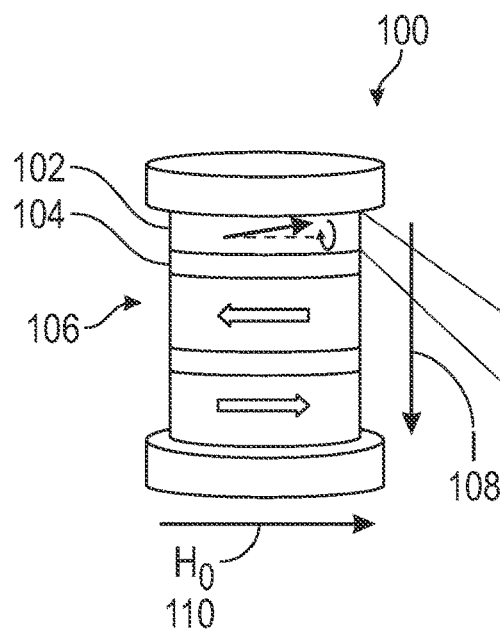
FIG. 1 is an isometric view of a spin torque oscillator (STO)

The present disclosure is directed to the use of a spin torque oscillator (STO), or an array or stack of STOs, in a lab-on chip (LOC) solution for polymerase chain reaction (PCR) operations for amplification of deoxyribonucleic acid (DNA). The details of PCR amplification of DNA, while not described in detail herein, are known to those of skill in the art.

A LOC is a device that integrates at least one laboratory function onto a single integrated circuit (IC). ICs are small and use small amounts of power. LOC solutions provide automation for processing samples on a small scale, such as fluid samples in very small amounts down to picoliters. LOCs can use microfluidic manipulation of small droplets of fluid to move the fluid around a reaction chamber on the chip, such as by the use of electrowetting of other processes.

Multiple LOC solutions for PCR operation are known. As the size of ICs used for LOCs, and the LOCs themselves, continue to shrink, certain processes that are used in LOCs become increasingly more difficult to scale. For example, heating is used extensively in PCR solutions in LOCs.

As the scale of LOCs for PCR functions drop down to the 10-20 micron size, typical heating solutions become unworkable. For example, for a reaction chamber on the size of about 200 microns square, heating solutions include resistive heating elements, microstrip lines, and the like. For larger processes, additional heating elements may be practical, such as microwave ovens or other traditional heating solutions. However, on the very small scale of current LOCs, with reaction chambers of 10 microns or even smaller, the heating solutions discussed above are not capable of discriminating heating on such a small scale. Current microwave strip lines are on a size order of about 2000 microns, which already reduces the effectiveness of heating only a portion of a reaction chamber.

It should be noted that the same reference numerals are used in different figures for same or similar elements. It should also be understood that the terminology used herein is for the purpose of describing embodiments, and the terminology is not intended to be limiting. Unless indicated otherwise, ordinal numbers (e.g., first, second, third, etc.) are used to distinguish or identify different elements or steps in a group of elements or steps, and do not supply a serial or numerical limitation on the elements or steps of the embodiments thereof. For example, "first," "second," and "third" elements or steps need not necessarily appear in that order, and the embodiments thereof need not necessarily be limited to three elements or steps. It should also be understood that, unless indicated otherwise, any labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," "intermediate" and the like are used for convenience and are not intended to imply, for example, any particular fixed location, orientation, or direction. Instead, such labels are used to reflect, for example, relative location, orientation, or directions. It should also be understood that the singular forms of "a," "an," and "the" include plural references unless the context clearly dictates otherwise.

Figure 2:
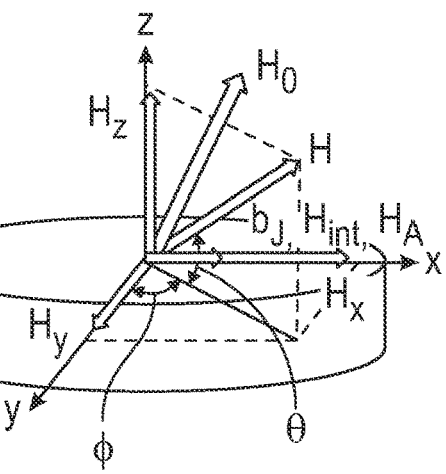
FIG. 2 is a diagram shown precession and details of a free layer of the STO of FIG. 1.

A spin torque oscillator (STO) 100 is shown in FIG. 1. A STO is a quantum device that includes a free layer 102, a tunnel barrier 104, and a fixed layer 106. An STO takes advantage of the electron spin torque effect. When a direct current (DC) 108 is passed through the device 100, the free layer 102 begins to precess and emit electromagnetic radiation. The precession of the free layer 102 can be tuned by the dimensions of the free layer 102 and the magnitude of the current 108. Further details of the precession are shown in FIG. 2. When designed with the right specifications, and using the right current, an STO such as STO 100 can emit microwaves.

Figure 3:
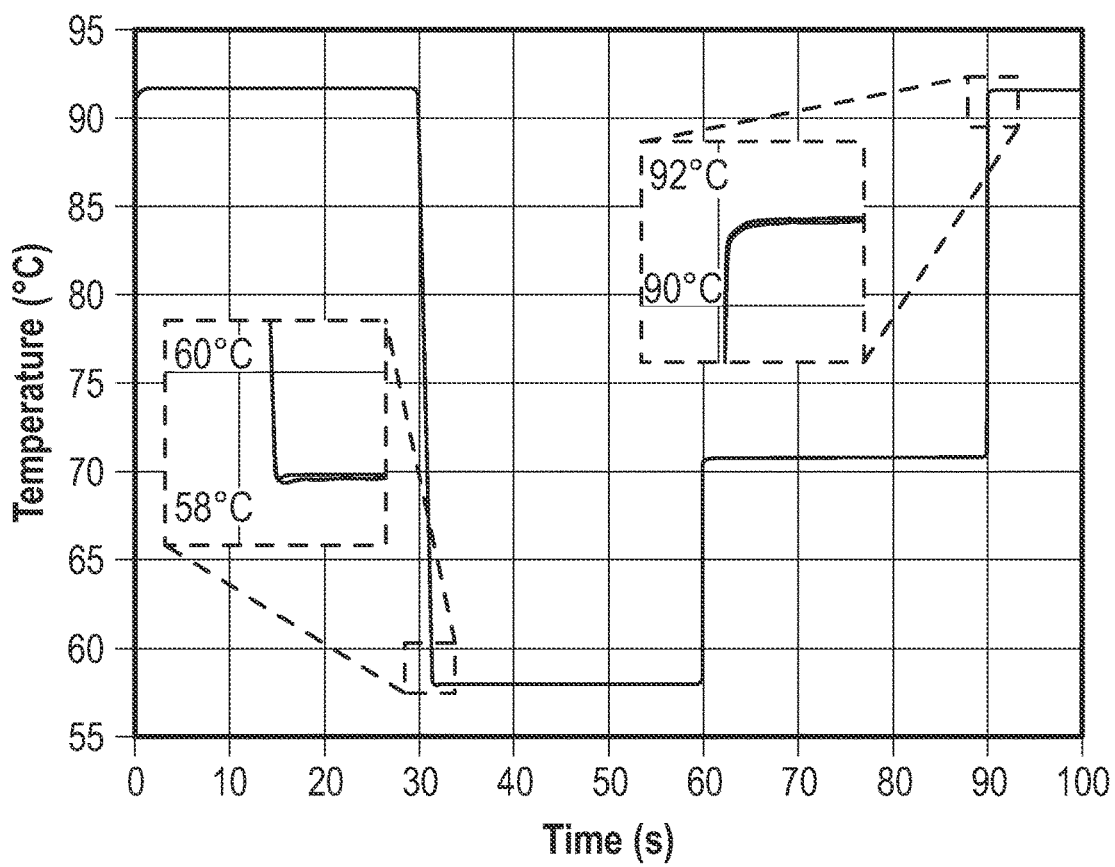
FIG. 3 is a diagram of a thermal cycling profile of a representative polymerase chain reaction (PCR) processing.

PCR processing uses several different heat levels, for example denaturing at about 92-96° C., annealing at about 50-65° C., and extension/elongation at about 70-80° C. A sample thermal cycling profile is shown in FIG. 3. For reference, an amount of fluid being heated in a PCR LOC solution may be on the order of 1.2 nanoliters (nL). For a 1.2 nL droplet size, for PCR processing, to heat 1.2 nL:

$$q=cm\Delta T$$

Where q=amount of thermal energy in Joules, c=heat capacity of water (about 4.184 J/gC), m=mass, and $\Delta T$ is the temperature change.

For heating steps of 13° C. and 21° C., the amount of energy to heat 1.2 nL of water is:

6.54 e-5 J for 13° C.
1.64 e-4 J for 21° C.

Heating rates for PCR processing should be quite short. For shorter cycling and therefore quicker PCR cycle times, heating of 13° C. in eight seconds, and heating of 21° in 13 seconds would use total power of:

8.12 microWatts ($\mu$W) for 21° C. in 13 seconds
8.17 $\mu$W for 13° C. in 8 seconds Therefore, about 8 $\mu$W of heating will be used. At about 20% efficiency of microwave absorption in water, stable power from STOs for up to 13 seconds of about 40 $\mu$W is therefore used for an STO in an LOC.

Figure 4:
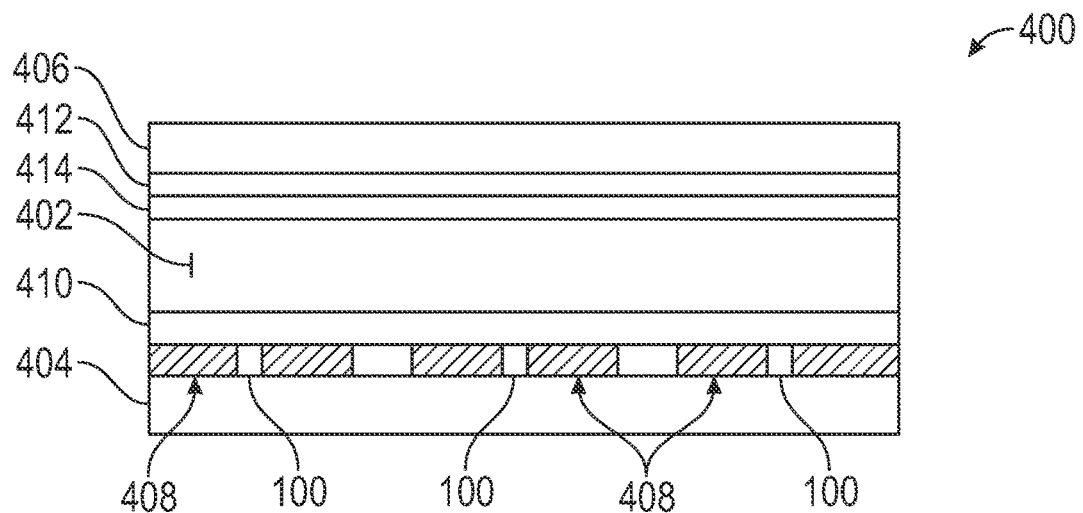
FIG. 4 is a side cross section view of a lab on chip according to an embodiment of the present disclosure.
Figure 5:
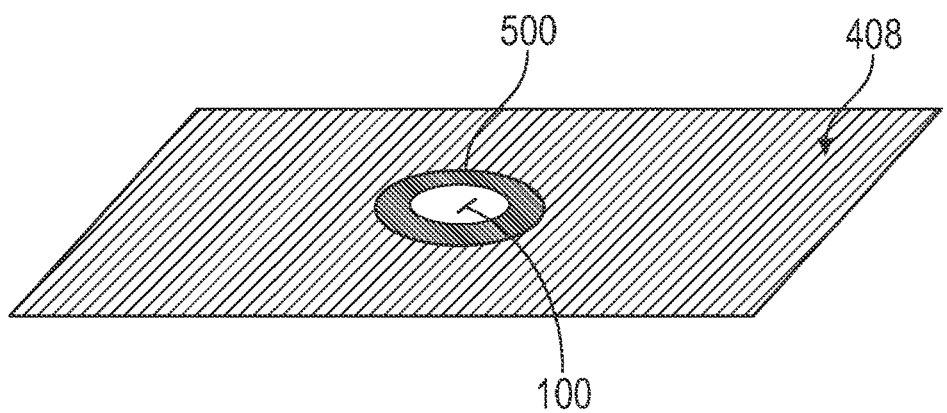
FIG. 5 is a perspective view of an STO arrangement according to an embodiment of the present disclosure.
Figure 6:
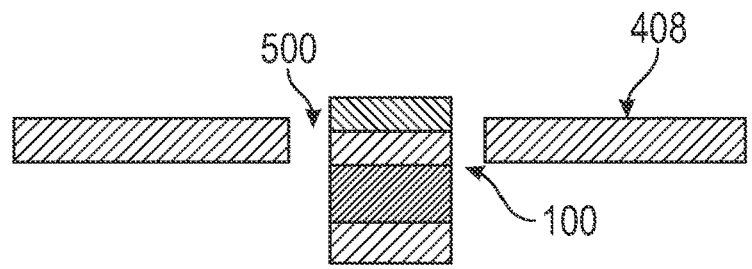
FIG. 6 is a side cross section view of the STO arrangement of FIG. 5.
Figure 7:
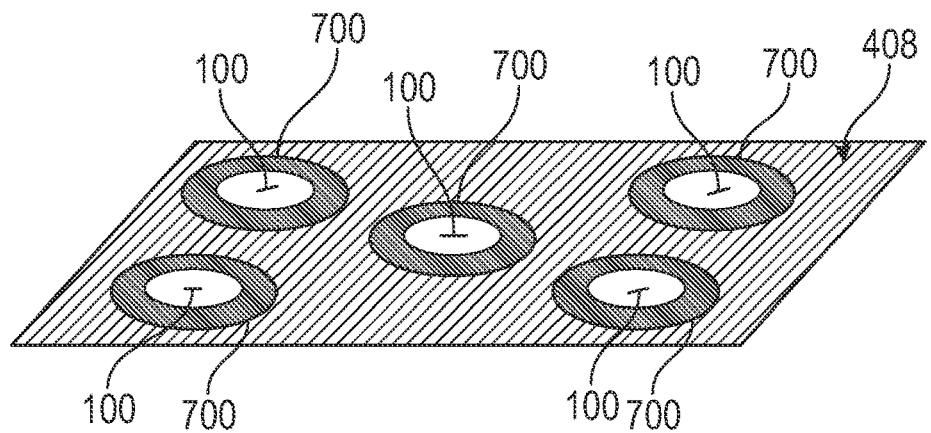
FIG. 7 is a perspective view of an STO arrangement according to an embodiment of the present disclosure.
Figure 8:
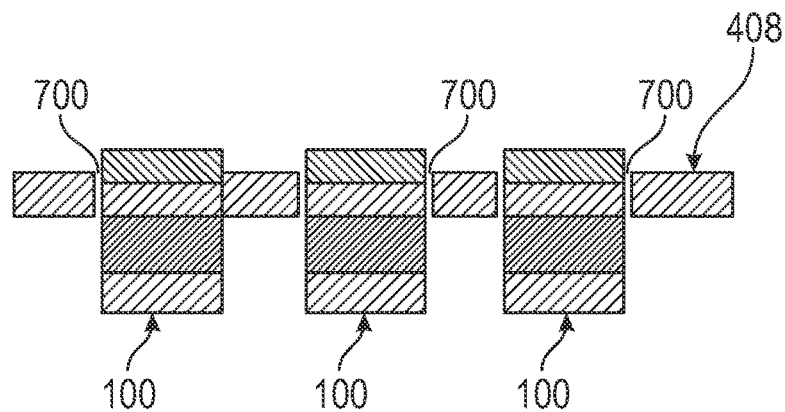
FIG. 8 is a side cross section view of the STO arrangement of FIG. 7.
Figure 9:
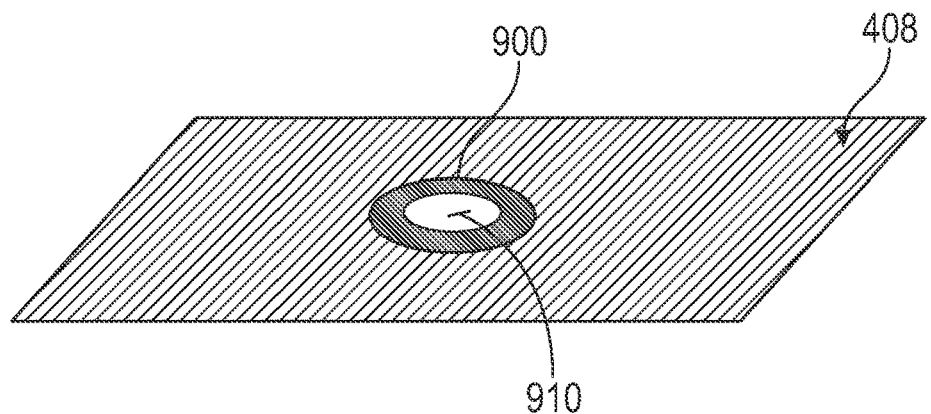
FIG. 9 is a perspective view of an STO arrangement according to an embodiment of the present disclosure.
Figure 10:
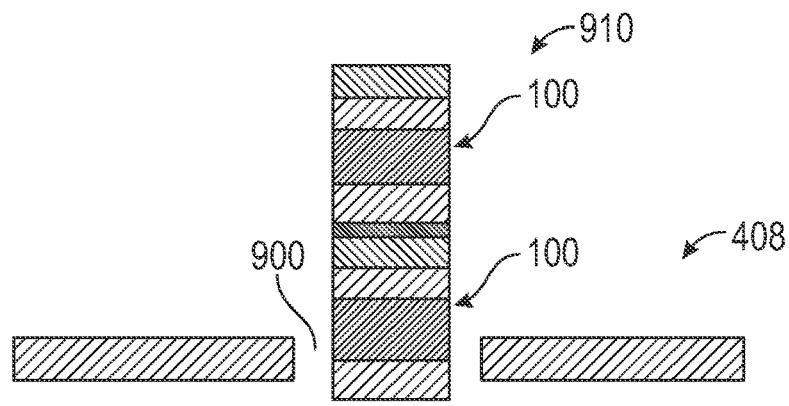
FIG. 10 is a side cross section view of the STO arrangement of FIG. 9.

A diagram of one embodiment 400 of an LOC employing STOs as heating elements is shown in side section view in FIG. 4. Perspective views of control electrodes and embodiments of STO positions and quantities are shown in FIGS. 5, 7, and 9. Section views of the FIGS. 5, 7, and 9 are shown in FIGS. 6, 8, and 10, respectively, and are discussed further below.

LOC 400 includes a reaction chamber 402. Reaction chamber 402 may be covered or uncovered. In this embodiment, a bottom plate 404 and a top plate 406 provide the upper and lower sections of the LOC 400. Control electrodes 408 are positioned between bottom plate 404 and a hydrophobic insulation layer 410. A ground electrode 412 is positioned between top plate 406 and hydrophobic insulation layer 414. STOs 100 are positioned in control electrodes 408. When a drop of fluid is over an STO, the STO is activated by passing a current through it. The STO then emits microwaves. These microwaves excite some of the water molecules and the fluid heats up.

Thermal cycling to perform a complete PCR processing may be used within the reaction chamber effected by the heating and subsequent cooling of the LCO reaction chamber. Cooling of small volumes is usually effected through ambient chamber temperature since the amounts of solution are very small, but cooling could also be implemented between heating cycles without departing from the scope of the disclosure.

FIG. 5 is a perspective view of a control electrode 408 using a single STO 100 positioned in a center of the electrode 408. To accommodate the STO 100, a hole 500 is made in the electrode 408. As shown in side section view in FIG. 6, the STO 100 may sit fully in the hole 500, or may protrude from the hole 500, without departing from the scope of the disclosure.

FIG. 7 is a perspective view of a control electrode 408 using an array of STOs 100 positioned in any desired configuration in the control electrode 408. As shown in FIG. 7, an array of five STOs 100 are positioned in five holes 700 in a cross pattern in the electrode 408. To accommodate the STOs 100, holes 700 are made in the electrode 408. As shown in side section view in FIG. 8, the STOs 100 may sit fully in the holes 700, or may protrude from the holes 700, without departing from the scope of the disclosure.

FIG. 9 is a perspective view of a control electrode 408 using a stacked STO 910 comprising at least two STOs 100 stacked on top of each other. The stacked STO 910 is positioned in one embodiment at a center of the electrode 408. To accommodate the stacked STO 910, a hole 900 is made in the electrode 408. As shown in side section view in FIG. 10, the stacked STO 910 protrudes from the hole 900, although a configuration with the stacked STO 910 may be accommodated nearly fully or fully within the hole 900 without departing from the scope of the disclosure.

It should further be understood that an array of STOs such as that shown in FIGS. 7-8 may use stacked STOs such as those shown in FIGS. 9-10 to form an array of stacked STOs. One advantage of using stacked STOs is to assist in agitation of the liquid as it moves in the vicinity of the stacked STOs. When multiple STOs are used, the STOs will be employed in phase to heat the liquid, unless each individual STO is employed for specific area heating.

In addition, a segmented micro-array is used in one embodiment to move fluid around the grid with electrowetting. Heating zones at different areas of a reaction chamber may be used by adjusting the arrangement of STOs, arrays of STOs, or stacked STOs such as are shown in FIGS. 5-10.

Leads for applying a bias current to the electrodes or a bias current to the STOs are not shown. One of skill in the art will readily understand the placement and operation of such leads.

Figure 11:
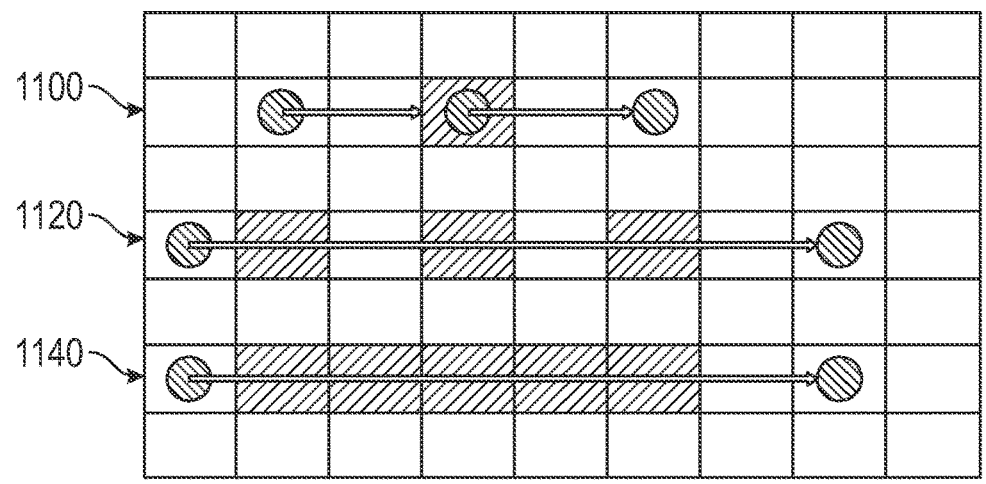
FIG. 11 is a top view of a reaction chamber surface with various processing operations according to embodiments of the present disclosure shown.

A series of sample grid patterns are shown in FIG. 11. The grid areas that are shaded in FIG. 11 are grid areas employing STOs. Three examples are shown, at 1100, 1120, and 1140.

At 1100, a single drop of fluid moves onto a square with the STO and stops. It is heated and then moves off the square once the desired temperature is reached.

At 1120, a single drop travels at a constant speed through a series of STO heater grids. This configuration achieves either a constant heating rate, or if the speed of travel of the drop is slow enough, a three temperature heating cycle (such as for PCR).

At 1140, a single trop travels through multiple squares with an STO heater, heater stack, or heater array. This is similar to 1120 except every stage is heated. Each stage may heat the same amount, or the configuration may be varied to generate a heating profile.

In another embodiment, STOs in the various configurations are tuned to a microwave frequency to excite additives to the fluid being subjected to the PCR process in a LOC. Instead of using the microwaves generated by the STOs to heat water molecules, a frequency that excites magnetic nano particles (NP) is used in one embodiment. The microwave frequency is chosen based on the material of the NP and the size thereof. Heating additive NPs provides additional degrees of freedom in STO design. Further, such use decouples the design space from heating just water, allowing for other fluid uses.

In another embodiment, conductive or even lossy dielectric particles are used to increase absorption of microwave energy generated by the STOs. Once again, the microwave frequency used depends on the material of the NP and the size thereof. This also provides additional degrees of freedom in STO design, and also decouples the design space from heating just water, allowing for other fluid uses.

While STOs have been discussed, other locally generated microwave sources may be used in other embodiments. For example, a single field effect transistor (FET) oscillator could be used to generate microwave particles. Alternatively, inductorless versions using a capacitior or diode in place of an inductor may be used. For example, generating 8 µW at 3 Volts DC, a FET sustaining an rf drain current of roughly 3 uA would suffice.

Another alternative is a three stage ring oscillator. Spin Hall Oscillators (SHOs) are another type of nanooscillator that can be used to generate microwaves, similarly to an STO. The Hall effect is used to direct electrons with desired spin toward an adjacent magnetic layer. Precession is induced in the magnetic layer.

Yet another alternative includes combining magnetoresistive devices, such as magnetic tunnel junctions, giant magnetoresistive devices, and/or Hall devices in a three-terminal STO/SHO. Such a configuration provides an increase in the amount of power that can be generated by either alone.

Figure 12:
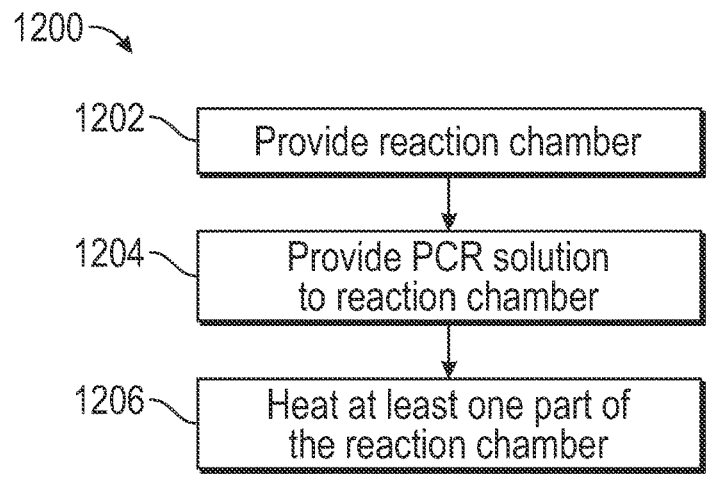
FIG. 12 is a flow chart diagram of a method according to an embodiment of the present disclosure.

A method 1200 of heating a polymerase chain reaction (PCR) solution in a lab on a chip (LOC) is shown in flow chart diagram in FIG. 12. Method 1200 comprises providing a reaction chamber on the LOC in block 1202, providing the solution to the reaction chamber in block 1204, and heating at least one part of the reaction chamber of the LOC in block 1206. The heating of the at least one part of the reaction chamber is performed using at least one spin torque oscillator (STO) configured to heat the PCR solution. Thermal cycling to perform a complete PCR processing may be used within the reaction chamber effected by the heating and subsequent cooling of the LCO reaction chamber. Cooling of small volumes is usually effected through ambient chamber temperature since the amounts of solution are very small, but cooling could also be implemented between heating cycles without departing from the scope of the disclosure.

Typical PCR solutions are known in the art, and typically comprise a number of components and reagents in solution. One such PCR solution includes a DNA template, a DNA polymerase, DNA primer(s), nucleotides, a buffer solution, and cations, although it should be understood that this is just an example and a PCR solution may be any type of solution amenable to the PCR process without departing from the scope of the disclosure.

Heating is accomplished in various embodiments using a single STO emitting microwaves, an array of STOs emitting microwaves, a stack of STOs emitting microwaves, or a combination thereof, including an array of stacked STOs. Heating at least one part of the reaction chamber comprises heating a plurality of zones, each zone heated by an individual STO, an array of STOs, a stack of STOs, an array of a stack of STOs, or some combination thereof.

In some embodiments, the solution may include conductive particles susceptible to heating with the microwaves, or combining magnetic nanoparticles susceptible to heating with the microwaves.

The LOC embodiments described herein may be a part of a larger system of a series of LOCs, controlled or operated by an operating system and software, hardware, firmware, or a combination thereof for effecting the processing using the LOC. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational processes to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The above-disclosed subject matter is to be considered illustrative, and not restrictive, and the appended claims are intended to cover all such modifications, enhancements, and other embodiments, which fall within the true scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A microfluidic device for polymerase chain reaction (PCR) processing, comprising:
   a platform with a microstructure with at least one reaction chamber; and
   a heating element for at least a part of the at least one reaction chamber, the heating element comprising at least one spin torque oscillator (STO) configured to heat the at least a part of the at least one reaction chamber to one or more temperatures for PCR processing.

2. The microfluidic device of claim 1, wherein the heating element comprises an array of STOs.

3. The microfluidic device of claim 2, wherein the array of STOs comprises an array of individual STOs.

4. The microfluidic device of claim 2, wherein the array of STOs comprises and array of stacked STOs.

5. The microfluidic device of claim 1, wherein the heating element comprises a stack of STOs.

6. The microfluidic device of claim 1, wherein the reaction chamber comprises a plurality of zones, each zone heated by an individual STO.

7. The microfluidic device of claim 1, wherein the reaction chamber comprises a plurality of zones, each zone heated by an array of STOs.

8. The microfluidic device of claim 1, wherein the reaction chamber comprises a plurality of zones, each zone heated by a stack of STOs.

9. A method of heating a polymerase chain reaction (PCR) solution in a lab on a chip (LOC), comprising:
   providing a reaction chamber on the LOC;
   providing the PCR solution to the reaction chamber; and
   heating at least one part of the reaction chamber of the LOC using at least one spin torque oscillator (STO) configured to heat the PCR solution.

10. The method of claim 9, wherein heating is accomplished using a single STO emitting microwaves.

11. The method of claim 9, wherein heating is accomplished using an array of STOs emitting microwaves.

12. The method of claim 9, wherein heating is accomplished with a stack of STOs emitting microwaves.

13. The method of claim 9, wherein heating at least one part of the reaction chamber comprises heating a plurality of zones, each zone heated by an individual STO.

14. The method of claim 9, wherein heating at least one part of the reaction chamber comprises heating a plurality of zones, each zone heated by an array of STOs.

15. The method of claim 9, wherein heating at least one part of the reaction chamber comprises heating a plurality of zones, each zone heated by a stack of STOs.

16. The method of claim 9, wherein providing the PCR solution comprises combining conductive particles susceptible to heating with the microwaves into the PCR solution.

17. The method of claim 9, wherein providing the PCR solution comprises combining magnetic nanoparticles susceptible to heating with the microwaves into the PCR solution.

18. A device, comprising:
- a reaction chamber for polymerase chain reaction (PCR) processing of deoxyribonucleic acid (DNA); and
- a heating element for at least a part of the reaction chamber, the heating element comprising at least one spin torque oscillator (STO) configured to heat the at least a part of the reaction chamber to one or more temperatures for PCR processing.

19. The device of claim 18, wherein the heating element comprises an array of STOs.

20. The device of claim 18, wherein the heating element comprises a stack of STOs.

* * * * *

UNITED STATES PATENT AND TRADEMARK OFFICE
CERTIFICATE OF CORRECTION

PATENT NO. : 11,654,436 B2
APPLICATION NO. : 17/397162
DATED : May 23, 2023
INVENTOR(S) : Tim Rausch et al.

It is certified that error appears in the above-identified patent and that said Letters Patent is hereby corrected as shown below:

In the Claims

Column 8, Claim 4, Line 33, please replace the word "and" with the word --an--.

Signed and Sealed this
Fifth Day of September, 2023

Katherine Kelly Vidal
*Director of the United States Patent and Trademark Office*